United States Patent
Dorsey

[19]
[11] Patent Number: 6,158,435
[45] Date of Patent: Dec. 12, 2000

[54] PESSARY

[76] Inventor: Denis P. Dorsey, 51 Rain Lily Rd., Levittown, Pa. 19056

[21] Appl. No.: 09/371,583

[22] Filed: Aug. 10, 1999

Related U.S. Application Data

[60] Provisional application No. 60/100,287, Sep. 14, 1998.

[51] Int. Cl.$^7$ ...................................................... A61F 6/06
[52] U.S. Cl. ............................................ 128/830; 128/834
[58] Field of Search ..................................... 128/830–841

[56] References Cited

U.S. PATENT DOCUMENTS

| | | | |
|---|---|---|---|
| 2,574,767 | 11/1951 | Stubbs | 128/834 |
| 4,823,814 | 4/1989 | Drogendijk | 128/834 |
| 5,771,899 | 6/1998 | Martelly | 128/834 |

OTHER PUBLICATIONS

Bioteque America, Inc.; "Silicone Pessary Product Line"; Undated; 1 Page.

Bioteque America, Inc.; "Silicone Oval Pessary"; Undated; 1 Page.

David Scott Miller, M.D.; "Contemporary Use of the Pessary", 1992; Gynecology and Obstetrics, vol. 1, pp. 1–12.

*Primary Examiner*—Michael A. Brown

[57] ABSTRACT

A pessary for vaginal use that prevents rotation after insertion is disclosed. An oval shape prevents rotation of the pessary once installed and a novel unitary molded structure with different hardnesses of biocompatible material eliminates the use of wire inserts that can become exposed and injure the user while facilitating folding of the pessary during insertion and removal. Further embodiments add an inner membrane to aid in controlling uterine prolapse and a novel raised portion or porch to support the urethra and control incontinence.

10 Claims, 4 Drawing Sheets

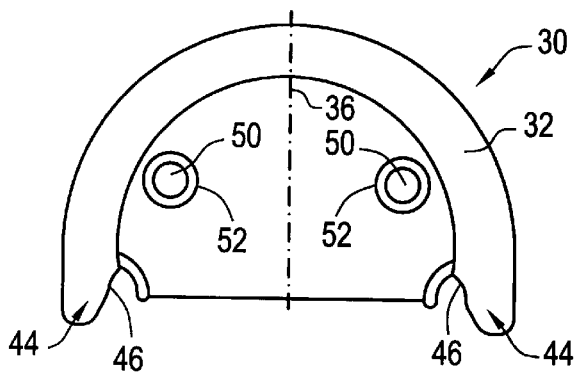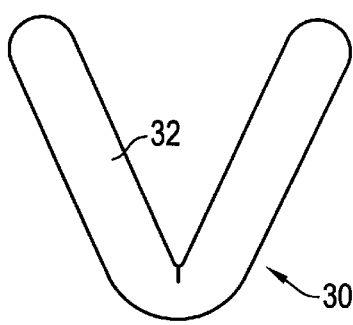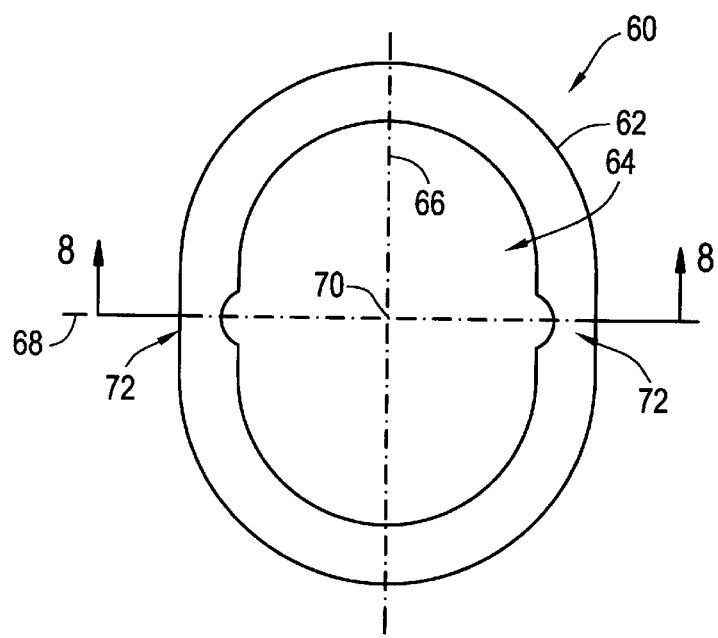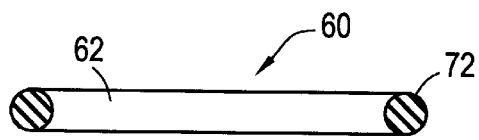

PESSARY

This application claims the benefit of U.S. Provisional Application No. 60/100,287, filed Sep. 14, 1998.

BACKGROUND OF THE INVENTION

1. Field of the Invention

The present invention relates to the field of medical devices. More specifically, the invention relates to a pessary device and method that uses a non-circular shape to prevent rotation within the vagina, resilient portions to define the fold axis, and other features to improve the performance of the pessary.

One type of pessary commonly used today is the ring pessary. A typical ring pessary has a toroidal outer ring, that is circular in cross section. In addition, some ring pessaries include an inner membrane support attached to the toroidal outer ring. Thus, the membrane support fills the circular inner cavity defined by the toroidal outer ring and acts as a sling that helps to support various degrees of prolapse. Generally, the membrane support includes passageways therethrough to facilitate the flow of bodily fluids through the pessary.

A ring type pessary is inserted into the vaginal cavity. Typically, the ring pessary is constructed of a resilient, though fairly rigid, biocompatible material such as medical grade silicone that permits the pessary to be folded for insertion.

To ensure that the pessary remains in position and does not become folded and, then, move out of position or exit the vagina, the pessary is designed to fold along a particular axis. In a typical ring pessary, the fold axis is created by forming the outer ring of the pessary around two semicircular, rigid wires or rods. The ends of the semicircular wires meet (without necessarily touching) at the fold axis and effectively prevent folding of the pessary in any other direction. In addition, many pessaries include a pair of small indentations formed in the inner portion of the toroidal outer ring at the fold axis. The indentations facilitate folding at the fold axis and help to identify the fold axis to the user.

Once inserted, the pessary is rotated ninety degrees to ensure that it is fully unfolded and properly positioned and to position the fold axis 20 lateral to the insertion/extraction direction. With the fold axis positioned at a ninety degree angle to the insertion/extraction direction, the pessary cannot fold and move out of position during normal use.

However, one problem associated with standard ring pessaries is that normal activity can cause the pessary to rotate in the vagina. When the pessary inadvertently rotates so that the fold axis is aligned with the insertion/extraction direction, the pessary may become inadvertently folded and move out of position. Such a result is undesirable because the ring pessary no longer provides adequate support and has a tendency to fold and fall out.

Thus, despite the use of the prior art features, there remains a need for a pessary that does not inadvertently rotate within the vagina during normal use.

Another problem associated with standard ring pessaries is associated with the use of the rigid wires to define the fold axis. Occasionally, the silicone, or other material, surrounding the wire will tear exposing the wire. The tear often occurs at the fold axis at the end of the wire. Therefore, a tear of the pessary often exposes the user of the pessary to a bare, rigid wire in a very sensitive area for the user which can result in injury.

Therefore, there is a need for a pessary that eliminates the rigid wire, but maintains the fold axis feature.

2. Description of Related Art

A pessary which utilizes stainless steel or a hard plastic material for the rigid inserts to define the fold axis is shown in U. S. Patent No. 5,771,899 (Martelly et al.) A sling support is also shown positioned at an acute angle to the axis of the main ring.

SUMMARY OF THE INVENTION

To achieve such improvements, the present invention provides a pessary that prevents inadvertent rotation and provides a fold axis without the use of wire within the pessary. To prevent rotation, the present invention provides a pessary having a non-circular outer shape. Once in place within the vagina, the non-circular pessary cannot rotate without an external force, such as one applied by the hand, rotating the pessary. To provide the fold axis, the present invention provides a pair of resilient portions of the outer member at the fold axis that are characterized by a more resilient area in the material as compared to the rest of the outer member. The durometer, or firmness, of the pessary is controlled during the manufacturing process to produce the resilient portions which define the fold axis.

One aspect of the present invention provides a pessary comprising an outer member defining a central opening and forming a non-circular or oval toroidal-like structure. The outer member has a substantially circular cross sectional shape in one embodiment. A longitudinal axis of the outer member extends through the center of the outer member and through the points of the outer member furthest from the center; a lateral axis of the outer member extends through the center of the outer member and through the points of the outer member nearest the center. The length of the outer member as measured along the longitudinal axis is longer than the width as measured along the lateral axis. The aspect ratio of the length to the width is preferably at least about 1.05. Once positioned in the vagina the non-circular pessary resists rotation due to the variation of the distance of the forces from the center and the orienting surfaces defined by the non-circular pessary.

Another aspect of the present invention provides a pessary that defines a fold axis without the use of embedded wire inserts. The outer member defines a resilient portion at the intersection of the outer member with the fold axis. Note that the resilient portion is equally useful with circular and non-circular pessaries. The resilient portion is an area of the outer member having a greater resilience (a lower durometer or shore; a greater softness) than the remainder of the outer member which is generally sufficiently stiff to prevent relatively easy folding.

Still another aspect of the invention provides a pessary having a non-circular outer member as described and having a fold axis that is the same as (positioned at) the lateral axis. This allows the pessary to be positioned in the resting, supporting position within the vagina with the relatively longer length directed front-to-back and the narrower width directed side-to-side which is the more natural position for the non-circular pessary within the pelvic cavity.

Alternative embodiments include or omit an inner membrane which fills the opening defined by the outer member. The inner membrane provides a sling for added support for various degrees of a uterine prolapse. Those embodiments which include the inner membrane preferably also provide passageways through the inner membrane to facilitate the flow of bodily fluids therethrough.

Further embodiments incorporate an additional support member in the form of a raised or enlarged section referred to as a "porch" at one of the longitudinal ends of the pessary. This "porch" is particularly efficacious in raising or repositioning the urethra and thereby preventing involuntary leakage of urine from the bladder, commonly known as incontinence. These with other objects and advantages of the present invention are pointed out with specificness in the claims annexed hereto and form a part of this disclosure. A full and complete understanding of the invention may be had by reference to the accompanying drawings and description of the preferred embodiments.

BRIEF DESCRIPTION OF THE DRAWINGS

The manner in which these objectives and other desirable characteristics can be obtained is explained in the following description and attached drawings in which:

FIG. 5 is a side elevational view of the first embodiment of the present invention in a folded position.

FIG. 6 is an end elevational view of the first embodiment of the present invention in a folded position.

FIG. 7 is a top elevational view of second embodiment of the present invention.

FIG. 8 is a sectional view taken along lines 8—8 in FIG. 7.

It is to be noted, however, that the appended drawings illustrate only typical embodiments of this invention and are therefore not to be considered limiting of its scope, for the invention may admit to other equally effective embodiments.

DESCRIPTION OF THE PRESENTLY PREFERRED EMBODIMENTS

Figure 1:
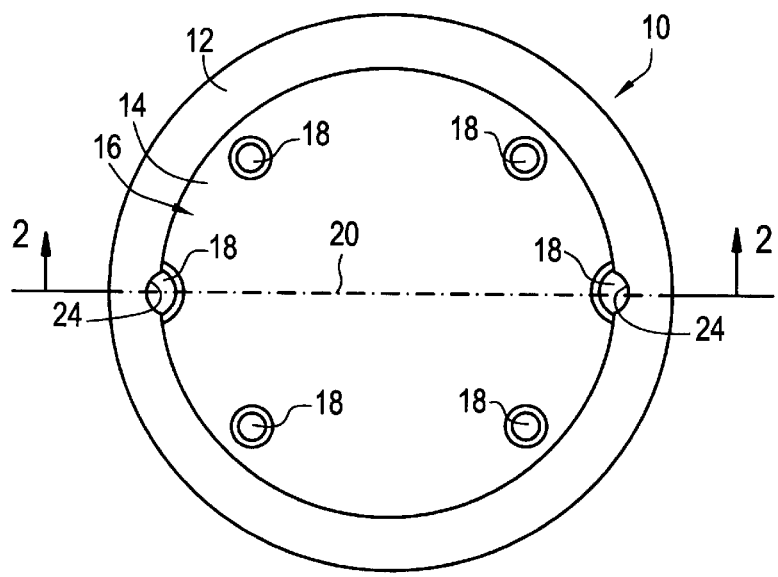
FIG. 1 is a top elevational view of a prior art ring pessary.
Figure 2:
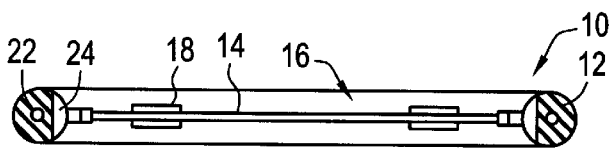
FIG. 2 is a sectional view taken along lines 2—2 in FIG. 1.

An example of a typical prior art ring pessary 10 commonly used today is shown in FIGS. 1 and 2. A typical ring pessary 10 has a toroidal outer ring 12, that is circular in cross section (See FIG. 1). In addition, some ring pessaries include an inner membrane wall 14 attached to the outer ring 12. The periphery of the membrane wall 14 is typically attached to the outer ring 12 at the smallest inner diameter defined by the outer ring 12. Thus, the membrane wall 14 fills the circular inner cavity 16 defined by the outer ring 12 and acts as a sling that helps to support degrees of prolapse. Generally, the membrane wall 14 includes passageways 18 therethrough to facilitate the flow of bodily fluids through the pessary 10.

A ring type pessary 10 is inserted into the vaginal cavity. Typically, the pessary 10 is constructed of a resilient, though fairly rigid, silicone that permits the pessary 10 to be folded for insertion. Generally, the pessary 10 is inserted using the hands of the patient or the doctor. It is folded with the leading edge of the formed crescent pointing downward. The pessary 10 is then inserted into the vagina.

To ensure that the pessary 10 remains in position and does not become folded and, then, move out of position or exit the vagina, the pessary 10 is designed to fold along a particular axis 20. In a typical ring pessary 10, the fold axis 20 is created by forming the outer ring 12 of the pessary 10 around two semicircular, rigid wires or rods 22. The ends of the semicircular wires or rods 22 meet (without necessarily touching) at the fold axis 20 and effectively prevent folding of the pessary 10 in any other direction. In addition, many pessaries include a pair of small indentations 24 formed in the inner portion of the outer ring 12 at the fold axis 20. The indentations 24 facilitate folding at the fold axis 20 and help to identify the fold axis 20 to the user.

Once inserted, the pessary 10 is rotated ninety degrees to ensure that it is fully unfolded and properly positioned and to position the fold axis 20 lateral to the insertion/extraction direction. With the fold axis 20 positioned at a ninety degree angle to the insertion/extraction direction, the pessary 10 cannot fold and move out of position during normal use.

However, one problem associated with standard ring pessaries is that normal activity can cause the pessary 10 to rotate in the vagina. When the pessary 10 inadvertently rotates so that the fold axis 20 is aligned with the insertion/extraction direction, the pessary 10 may become folded and move out of position. Such a result is undesirable because the pessary no longer provides adequate support and has a tendency to fold and fall out.

Thus, despite the use of the prior art features, there remains a need for a pessary that does not inadvertently rotate within the vagina during normal use.

Another problem associated with standard ring pessaries is associated with the use of the rigid wires or rods 22 to define the fold axis 20. Occasionally, the silicone, or other material, surrounding the wire or rod 22 will tear exposing the wire or rod 22. The tear often occurs at the fold axis 20 at the end of the wire or rod 22. Often, the tear occurs during insertion or extraction of the pessary 10 while the pessary 10 is in a folded position and the area near the ends of the wire or rod 22 is stretched and with the wire or rod 22 end pressing against the thinned, stretched material. Therefore, a tear of the pessary 10 often exposes the user of the pessary 10 to a bared, rigid wire or rod 22 in a very sensitive area for the user which can result in injury.

Therefore, there is a need for a pessary that eliminates the rigid wire, but maintains the fold axis feature.

The present invention generally provides a pessary that prevents inadvertent rotation and provides a fold axis without the use of wire within the pessary. To prevent rotation, the present invention provides a pessary having a non-circular outer shape. Once in place within the vagina, the non-circular pessary cannot rotate without an external force, such as one applied by the hand, rotating the pessary. To provide the fold axis, the present invention provides a pair of resilient portions of the outer member at the fold axis that are characterized by a more resilient material as compared to the rest of the outer member. The durometer, or firmness, of the pessary is controlled during the manufacturing process to produce the resilient portions which define the fold axis.

Figure 3:
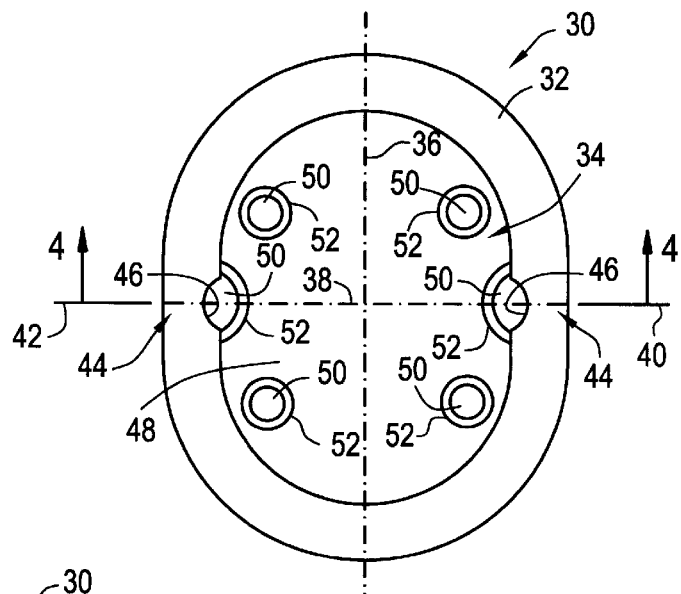
FIG. 3 is a top elevational view of a first embodiment of the present invention.
Figure 4:
FIG. 4 is a sectional view taken along lines 4—4 in FIG. 3.

FIGS. 3 and 4 are top elevational and sectional views respectively of the present invention. The pessary 30 is formed of an outer member 32 that is substantially circular in cross section, although other non-circular cross sectional shapes are acceptable and anticipated. Like the prior art, the pessary 30 forms a continuous band. However, unlike the prior art, the pessary 30 of the present invention is non-circular. In one preferred embodiment, shown in FIG. 3, the pessary 30 has an oval, or racetrack, shape. Thus, the outer member 32 resembles a toroidal-like shape, except that the resulting shape is non-circular. The outer member 32 defines an opening 34 therethrough with the diameter of the cross section of the outer member 32 substantially constant. Thus, the outer periphery of the outer member 32 has approximately the same shape as the outer periphery of the opening 34 defined by the outer member 32.

Further, the outer member 32 preferably defines a longitudinal axis 36 through its center 38 extending through the points of the outer member 32 that are furthest from the center 38 (or, if the outer member 32 is nonsymmetrical, extending in the direction of the greatest length of the outer member 32). Preferably, the outer member 32 and the pessary 30 are symmetrical about the longitudinal axis 36.

A lateral axis 40 extends through the center 38 of the outer member 32 in a direction perpendicular to the longitudinal axis 36 in the embodiment shown in the figures (or, in a direction of the least width of the outer member 32). In other words, the lateral axis 40 extends linearly through the center 38 of the outer member 32 and through the points of the outer member 32 that are nearest the center 38. Preferably, the outer member 32 is symmetrical about tne lateral axis 40.

Accordingly, the outer member 32 defines a length measured along the longitudinal axis 36 and a width measured along the lateral axis 40. In the present invention, the length does not equal the width so that the outer member 32 is non-circular.

Consequently, when the non-circular pessary 30 is positioned in the vagina and rotated to the desired position, the vaginal walls press against the outer member 32 holding it in the predetermined rotational position. Unlike circular pessaries which are free to rotate due to the equal distribution of forces about the center 38 of the pessaries, the fact that the forces are directed radially only, and the absence of surfaces resistive to rotation, the present invention provides a distribution of the forces on the outer member 32 of the pessary 30 that are different distances from the center 38 of the outer member 32 and the pessary 30. Also, the non-circular shape of the present invention provides orienting surfaces that direct a portion of the forced on the pessary 30 in a direction other than toward its center 38 and that are, thus, resistive to the rotation of the pessary 30. The non-circular pessary 30 positioned in the vagina is held by the vaginal walls and prevented from rotating.

To ensure that the pessary 30 does not rotate once properly positioned within the vagina, the length of the outer member 32 is substantially larger than its width. Preferably, the aspect ratio of the length to the width is at least about 1.05 and more preferably at least about 1.15. In one preferred embodiment, the length of the outer member 32 is about 10 mm longer than the width. The higher aspect ratio creates larger orienting surfaces and a greater variance in the distribution and vector direction of the forces about the center 38 of the pessary 30. However, the aspect ratio must be small enough that the pessary 30 is suitable for performing its supportive functions. The pessary 30 must provide a sufficient projected surface area, as shown in FIG. 3, that it may support a prolapse of the uterus.

Additionally, the outer member 32 is sized and adapted to be placed within the vagina and to support the patient's prolapse. Because people are of different sizes, the pessaries come in different sizes. Further, to facilitate placement of the pessary 30 within the vagina (and as previously discussed), the pessary 30 is adapted for folding during insertion and extraction. Preferably, the pessary 30 defines a fold axis 42 along which the pessary 30 may be folded exclusively. The pessary 30 is adapted to fold along the fold axis 42 only and to not fold in any other direction sufficiently for insertion or removal. Typically, the pessary 30 is formed of a biocompatable material, such as silicone, and is therefore somewhat resilient and bendable. However, the outer member 32 of the pessary 30 is generally sufficiently rigid to prevent a bending of the outer member 32 that is sufficient for the pessary 30 to be inserted or removed from the vagina, except as provided at the fold axis 42.

To provide for the selective bending and the fold axis 42, the pessary 30 may incorporate semicircular wires embedded within the outer member 32 as done in the prior art. In addition, the present invention may incorporate any other method of defining the fold axis 42 currently used in the prior art. However, in the preferred embodiment, the outer member 32 defines a pair of resilient portions 44 of the outer member 32, one at each area where the fold axis 42 intersects the outer member 32. The resilient portions 44 of the outer member 32 are areas of the outer member 32 where the material forming the outer member 32 is more resilient (has a lower durometer or shore; is softer) than the remainder of the outer portion. Thus, as used herein, the term "resilient portion" 44 means a portion of the outer member 32 that is relatively more resilient (has a lower durometer or shore; is softer) than the remainder of the outer member 32. The durometer, or firmness, of the pessary 30 is controlled during the manufacturing process to produce the resilient portions 44 which define the fold axis 42. The resiliency and length of the resilient portion 44 must be sufficient that it allows the outer member 32 to be bent. Note that the use of the resilient portions 44 to define the fold axis 42 is equally useful with circular or non-circular pessaries (i.e. regardless of the shape of the pessary 30).

As mentioned, the pessary 30 is inserted into or removed from the vagina while in a folded position with the formed crescent of the pessary 30 pointing downward and the leading edge of the formed crescent inserted first (FIGS. 5 and 6 show the pessary 30 in the folded position). Once placed in the desired position within the vagina, the resilient pessary 30 is allowed to unfold and is rotated ninety degrees to the resting position so that the fold axis 42 is perpendicular to its direction during insertion. The rotation of the pessary 30 to the resting position facilitates unfolding and proper positioning of the pessary 30. In addition, however, rotating the pessary 30 to the resting position with the fold axis 42 directed toward the wearer's legs helps to maintain the pessary 30 in position. During normal daily activities, the wearer's bending, moving, walking, lifting, and other motions push on the pessary 30. However, the unfolded pessary 30 is too large to pass from the vagina and is, therefore, maintained in the proper, resting (or supporting) position. However, if the fold axis 42 were aligned perpendicular to the resting position with the fold axis 42 directed perpendicular to the wearer's legs and toward the vaginal cavity, the pessary 30 may tend to fold during the normal daily motions and, thereby, move from the proper, supporting and from the vagina.

Preferably, the fold axis 42 is positioned at the lateral axis 40 as shown in FIG. 3 along the narrowest width of the pessary 30. Thus, when inserted, the pessary 30 initially unfolds, during insertion, with the longitudinal axis 36 directed toward the wearer's legs and the lateral and fold axes directed in a forward direction. The pessary 30 is then rotated ninety degrees so that the lateral and fold axes are directed toward the wearer's legs and longitudinal axis 36 is directed in a forward direction. Therefore, when in the resting position, the pessary 30 is positioned in the vagina with the longer portion directed front-to-back and the narrower portion directed side-to-side and fitting between the legs of the wearer. Such a positioning allows the pessary 30 to fit within the pelvic cavity better and provides a more natural positioning within the pelvic cavity for the pessary 30. Due to the natural positioning, inadvertent rotation of the pessary 30 is unlikely.

One embodiment of the present invention as shown in FIGS. 3 and 4, provides indentations 46 in the inner sides of the outer member 32 at the fold axis 42. The outer member 32 defines small indentations 46 at each point of intersection of the fold axis 42 with the inner portion of the outer member 32 (on each side of the outer member 32). The indentation 46 merely represents a thinned area of the outer member 32. By thinning the outer member 32 at the fold axis 42, the indentation 46 facilitates bending at the fold axis 42 because it weakens the area making the outer member 32 more resilient at the indentation 46. In addition, the indentation 46 helps to identify the fold axis 42 to the user so that the user knows where to fold the pessary 30.

The embodiment of FIGS. 3 and 4 provides an inner membrane 48 attached about its periphery to the outer member 32 filling the opening 34 defined by the outer member 32. The inner membrane 48 preferably attaches to the outer member 32 at the point nearest the center 38 of the pessary 30. Thus, the inner membrane 48 preferably lies in a plane that extends through the center 38 of the cross sectional area of the outer member 32 because the outer member 32 is preferably circular in cross section.

To allow fluid to pass through the inner membrane 48, the inner membrane 48 preferably defines at least one passageway 50 therethrough. The indentations 46 also may serve as passageways 50 through the inner membrane 48. Typically, a surrounding lip 52, or thickened portion, surrounds the inner membrane 48 to add strength to the inner membrane 48 and prevent its tearing at the passageways 50.

FIGS. 5 and 6 show the pessary 30 in a folded position.

Another embodiment of the pessary of the present invention is shown in FIGS. 7 and 8 that are top elevational and sectional views, respectively, of a pessary 60 that does not include indentations or an inner membrane. However, pessary 60 comprises an outer member 62 having a non-circular shape or oval shape. Outer member 62 is substantially circular in cross section. The outer member 32 defines an opening 64 therethrough as in the previous embodiments. Further, the outer member 62 preferably defines a longitudinal axis 66 and lateral axis 68 that intersect at center 70 extending through the points of the outer member 62 that are furthest from the center 70.

As in the previous embodiment, it is to ensure that the pessary 60 does not rotate once properly positioned within the vagina, the length of the outer member 62 is substantially larger than its width. Preferably, the aspect ratio of the length to the width is at least about 1.05 and more preferably at least about 1.15. Also, the pessary 60 is adapted for folding during insertion and extraction. Preferably, the pessary 30 defines a fold axis 68 along which the pessary 60 may be folded exclusively. This is accomplished as before with the area of outer member 62 adjacent the lateral or fold axis 68 being formed of a relatively softer biocompatible silicone than that which the remainder of outer member 62 is formed.

These softer or resilient portions 72 of outer member 62 are areas of outer member 62 where the material forming outer member 62 is more resilient (has a lower durometer or shore reading i.e., is softer) than the remainder of outer member 62. Thus, as used herein, the term "resilient portion" 72 means a portion of outer member 62 that is relatively more resilient, i.e., softer and more flexible than the remainder of outer member 62. The resiliency and length of the resilient portion 72 must be sufficient that it allows the outer member 62 to be bent.

Figure 9:
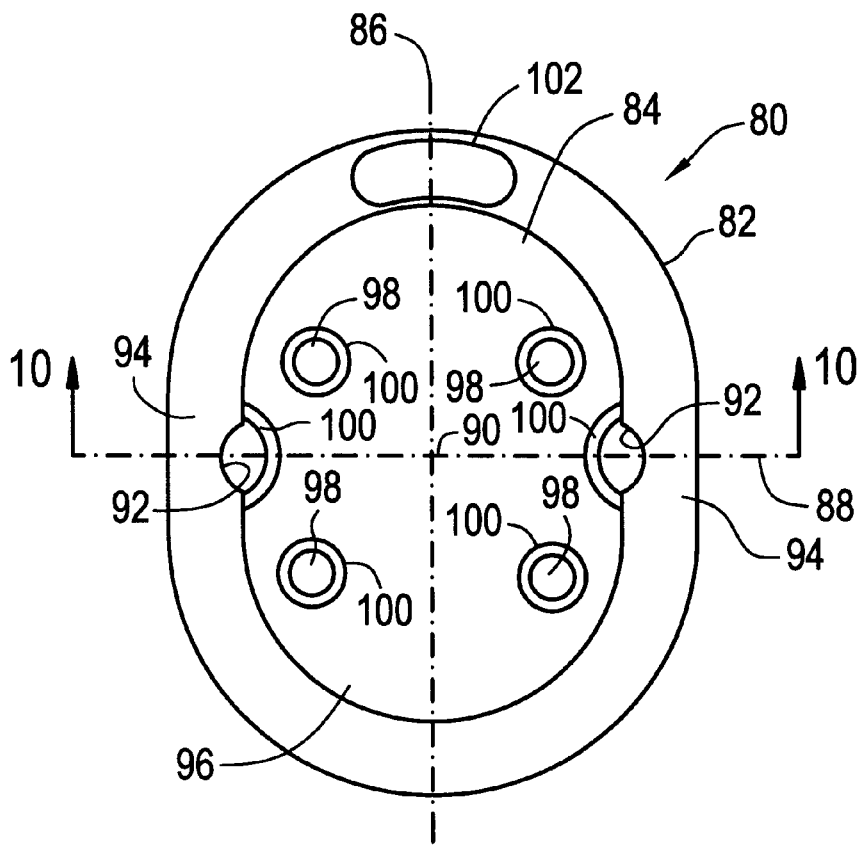
FIG. 9 is a top elevational view of a third embodiment of the present invention.
Figure 10:
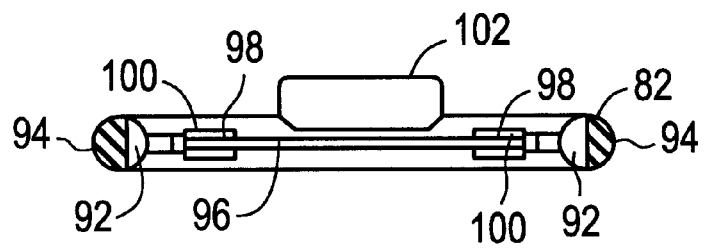
FIG. 10 is a sectional view taken along lines 10—10 in FIG. 9.

A third embodiment of the pessary of the present invention is shown in FIGS. 9 and 10 that are top elevational and sectional views, respectively, of pessary 80 that includes a raised or enlarged section referred to as a "porch" at one of the longitudinal ends of pessary 80. This "porch" is particularly efficacious in raising the urethra and thereby preventing involuntary leakage of urine from the bladder. As in the previous embodiments, pessary 80 comprises an outer member 82 having a non-circular shape or oval shape. Outer member 82 is substantially circular in cross section. The outer member 82 defines an opening 84 as in the previous embodiments. Further, the outer member 82 preferably defines a longitudinal axis 86 and lateral axis 88 that intersect at center 90 extending through the points of the outer member 82 that are furthest from the center 90.

As in the first embodiment, outer member 82 provides indentations 92 in the inner sides of outer member 82 at the fold or lateral axis 88. Indentations 92 merely represent a thinned area of outer member 82. By thinning outer member 82 at fold axis 88, indentations 92 facilitate bending at the fold axis 88 because it weakens the area making the outer member 82 more resilient at indentations 92. As in the previous embodiments, more resilient areas 94 are formed adjacent lateral fold axis 88 to facilitate folding of the pessary during insertion and removal.

The third embodiment of FIGS. 9 and 10 provides an inner membrane 96 attached about its periphery to outer member 82 as in the first embodiment. Inner membrane 96 includes a plurality of passageways 98 therethrough. A surrounding lip 100, or thickened portion, surrounds indentations 92 and passageways 98 to add strength to inner membrane 96 and prevent tearing at indentations 92 and passageways 98.

A final feature of pessary 80 is the formation of a raised portion or porch 102 on one of the longitudinal ends of pessary 80. Porch 102 is an arcuate raised portion on outer member 82 straddling longitudinal axis 86. Porch 102 is molded as a part of outer member 82 and is of the same relatively harder biocompatible silicone as the majority of outer member 82 in contrast to the softer, more resilient material of resilient areas 94. Porch 102 is designed and sized to aid in supporting the urethra. Pessary 80 is folded and inserted into the vagina as previously described. Pessary 80 is then rotated 90 degrees as in the other embodiments with porch 102 exerting pressure on the upper vaginal wall and urethra to aid in preventing incontinence.

Figure 11:
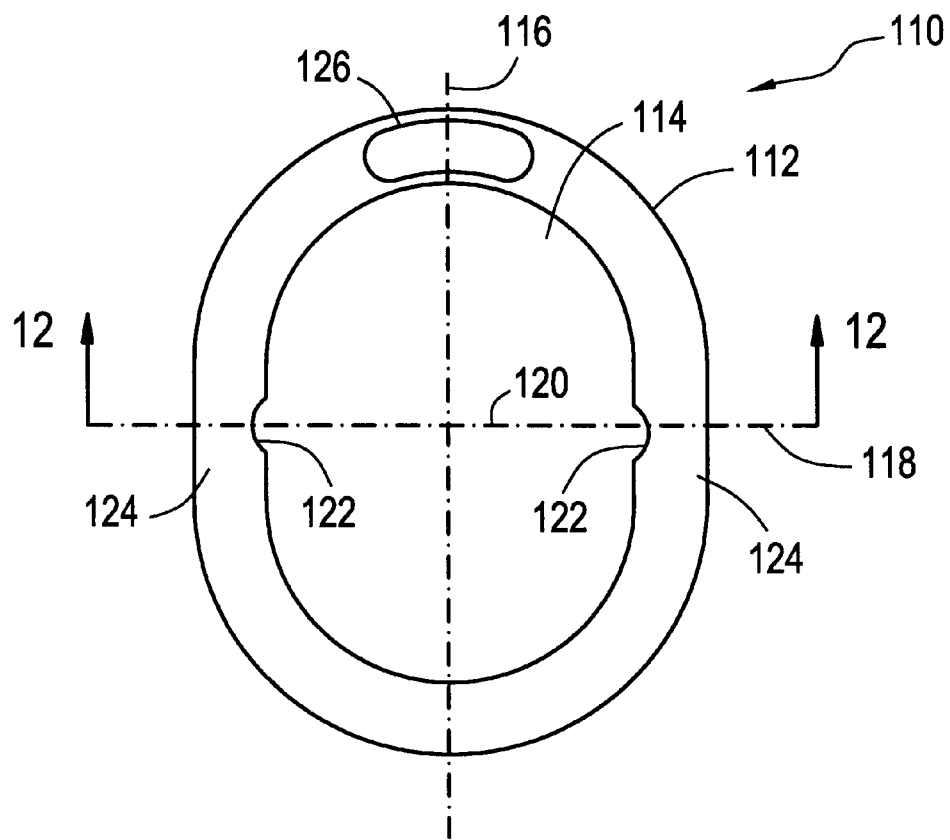
FIG. 11 is a top elevational view of a fourth embodiment of the present invention.
Figure 12:
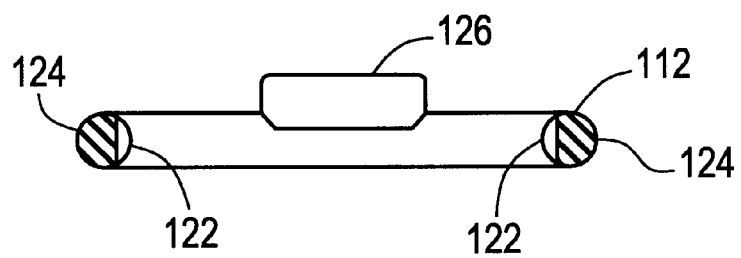
FIG. 12 is a sectional view taken along lines 12—12 in FIG. 11.

A fourth embodiment of the pessary of the present invention is shown in FIGS. 11 and 12 that are top elevational and sectional views, respectively, of pessary 110 that includes a raised or enlarged section referred to as a "porch" at one of the longitudinal ends of pessary 110. Pessary 110 is essentially the same as pessary 80 but without the inner membrane. As in the previous embodiments, pessary 110 comprises an outer member 112 having a non-circular shape or oval shape. Outer member 112 is substantially circular in cross section. The outer member 112 defines an opening 114 as in the previous embodiments. Further, the outer member 112 preferably defines a longitudinal axis 116 and lateral axis 118 that intersect at center 120 extending through the points of the outer member 112 that are furthest from the center 120.

As in the previous embodiments, outer member 112 provides indentations 122 in the inner sides of outer member 112 at the fold or lateral axis 118. Indentations 122 merely represent a thinned area of outer member 112. As in the previous embodiments, more resilient areas 124 are formed adjacent lateral fold axis 118 to facilitate folding of the pessary during insertion and removal.

A final feature of pessary 110 is the inclusion of a raised portion or porch 126 on one of the longitudinal ends of pessary 110 as in the previous embodiment. Porch 126 is an arcuate raised portion on outer member 112 straddling longitudinal axis 116. Porch 126 is identical in all respects to porch 102 of the previous embodiment and functions in the same manner.

My improved apparatus to provide a pessary that prevents rotation within the vagina and is easily folded and inserted without requiring the use of wire inserts and the methods of its application will be readily understood from the foregoing description. Furthermore, while the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the appended claims.

What is claimed is:

1. A pessary for treating uterine prolapse and urinary continence, comprising:
   an outer member constructed of a biocompatible material having a substantially oval shape and defining a single plane, said outer member having longitudinal and lateral axes; and,
   said outer member is formed of a more resilient biocompatible material adjacent said lateral axis and having a lower durometer number than said outer member biocompatible material to facilitate folding said outer member along said lateral axis.

2. A pessary for treating uterine prolapse and urinary continence according to claim 1 wherein said outer member includes:
   indentations formed in said more resilient biocompatible material along said lateral axis to facilitate folding along said lateral axis and aid a user in determining said lateral fold axis.

3. A pessary for treating uterine prolapse and urinary continence according to claim 2 wherein:
   said outer member preferably has an aspect ratio in the range of 1.05 to 1.15 to prevent rotation of said pessary within a wearer's vagina.

4. A pessary for treating uterine prolapse and urinary continence according to claim 3 wherein:
   said outer member includes an inner membrane to aid in controlling uterine prolapse.

5. A pessary for treating uterine prolapse and urinary continence according to claim 4 wherein:
   said inner membrane includes at least one passageway to facilitate passage of bodily fluids.

6. A pessary for treating uterine prolapse and urinary continence, comprising:
   an outer member constructed of a biocompatible material having a substantially oval shape and defining a single plane, said outer member having longitudinal and lateral axes;
   said outer member includes a porch on said outer member; and,
   said outer member is formed of a more resilient biocompatible material adjacent said lateral axis and having a lower durometer number than said outer member biocompatible material to facilitate folding said outer member along said lateral axis.

7. A pessary for treating uterine prolapse and urinary continence according to claim 6 wherein said outer member includes:
   indentations formed in said more resilient biocompatible material along said lateral axis to facilitate folding along said lateral axis and aid a user in determining said lateral fold axis.

8. A pessary for treating uterine prolapse and urinary continence according to claim 10 wherein:
   said outer member preferably has an aspect ratio in the range of 1.05 to 1.15 to prevent rotation of said pessary within a wearer's vagina.

9. A pessary for treating uterine prolapse and urinary continence according to claim 8 wherein:
   said outer member includes an inner membrane to aid in controlling uterine prolapse.

10. A pessary for treating uterine prolapse and urinary continence constructed of a biocompatible material according to claim 9 wherein:
    said inner membrane includes at least one passageway to facilitate passage of bodily fluids.

* * * * *